United States Patent [19]

Egan et al.

[11] Patent Number: 5,054,928

[45] Date of Patent: Oct. 8, 1991

[54] SYSTEM FOR COMPENSATING ANTENNA MEMBRANE DEFLECTION

[75] Inventors: Walter G. Egan, Woodhaven; Robert E. Ryan, Levittown, both of N.Y.; George P. Gayes, Port St. Lucie, Fla.

[73] Assignee: Grumman Aerospace Corporation, Bethpage, N.Y.

[21] Appl. No.: 493,815

[22] Filed: Mar. 15, 1990

[51] Int. Cl.⁵ .............................................. G01B 11/24
[52] U.S. Cl. .................................... 356/400; 356/369
[58] Field of Search ................ 356/399, 400, 401, 369

[56] References Cited

U.S. PATENT DOCUMENTS 4,672,196 6/1987 Canino .................................. 356/369

Primary Examiner—Samuel Turner
Attorney, Agent, or Firm—Pollock, VandeSande & Priddy

[57] ABSTRACT

Alignment of antenna radiating elements is monitored by diode lasers which have polarized light reflected from the body of the antenna toward a detector array. The array monitors displacement of polarized radiations from a diode laser corresponding to displacements of the antenna body. Signals from the array to electronically compensate for misalignment or may be utilized in a servo system for mechanically correcting misalignment.

7 Claims, 2 Drawing Sheets

5,054,928

SYSTEM FOR COMPENSATING ANTENNA MEMBRANE DEFLECTION

FIELD OF THE INVENTION

The present invention relates to antenna systems, and more particularly to a system for monitoring displacements of a deployable antenna membrane.

BACKGROUND OF THE INVENTION

A basic requirement for a space-based antenna is the precise alignment of the radiating elements and/or the reflector (the antenna figure). The alignment required is usually 0.1 of the wavelength or better. For an X-band system, this tolerance is 3 mm. There have been a number of alignment techniques proposed; and in general, a real time sensing system is to be preferred because of its adaptability to a servo system for an actively controlled correction of the antenna figure. A number of existing systems have the disadvantage of relying on fiber optic components which embrittle in space due to low temperatures and radiation.

In a deployable membrane antenna of the present assignee, a figure monitoring system was devised using three photogrammetric cameras that simultaneously photograph points on the flat membrane antenna. Then the photographic film is developed and the imagery analyzed photogrammetrically to determine the motion of the points. The procedure produces the required accuracy of 0.1 wavelength, but is limited by the frame rate of the camera. Further, the process is not done in real time.

The problem of alignment of large ground-based radio telescopes has been with us for many years. The ground-based alignments are facilitated by the presence of terra firma on which to locate instrumentation and easily accessible associated computer equipment. Of course, this is not possible in space.

BRIEF DESCRIPTION OF THE INVENTION

The proposed space-based alignment system of the present invention is a polarimetric system which generally involves sensing of displacement and/or angular position of selected targets on the antenna.

The system measures the polarized radiation scattered from a membrane using the polarized radiation from diode lasers. The location of the polarized reflection is monitored by a diode array, which physical arrangement will depend upon the positional sensitivity of the system. A sensitivity of ±0.1 mm or better is realizable.

A diode array which monitors polarized reflection has individual diodes energized in response to displacements of points on the antenna membrane, such as occurs when the antenna membrane undergoes vibration.

Information from the diode array undergoes analog-to-digital conversion and may then be utilized by a computer for electronically correcting for any deflection of a deployable antenna membrane from a planar position.

An advantage of using polarized radiation is that reflection of solar radiation or other laser radiation by the antenna may be selectively eliminated by the appropriate choice of geometry. This advantage is in addition to that gained by narrow band filtration of the desired reflected laser radiation wavelength at the detectors, and the fact that the system is energy efficient, using the most effective polarization in the reflection technique.

A further advantage of polarization is that any angular displacement of the point of reflection will be characterized by a rotation of the plane of polarization of the incident radiation.

The present invention utilizing polarized reflection is also applicable to parabolic antennas. Since data on antenna figure is available in real time, servo loops may be implemented to correct the figure as changes occur. Further, although the present invention will be discussed in terms of antenna membrane deflection, it should be realized that it is equally applicable to other fields, such as the monitoring of deflections in structural members, such as those existing in bridges and buildings.

BRIEF DESCRIPTION OF THE FIGURES

The above-mentioned objects and advantages of the present invention will be more clearly understood when considered in conjunction with the accompanying drawings, in which.

DETAILED DESCRIPTION OF THE INVENTION

Figure 1:
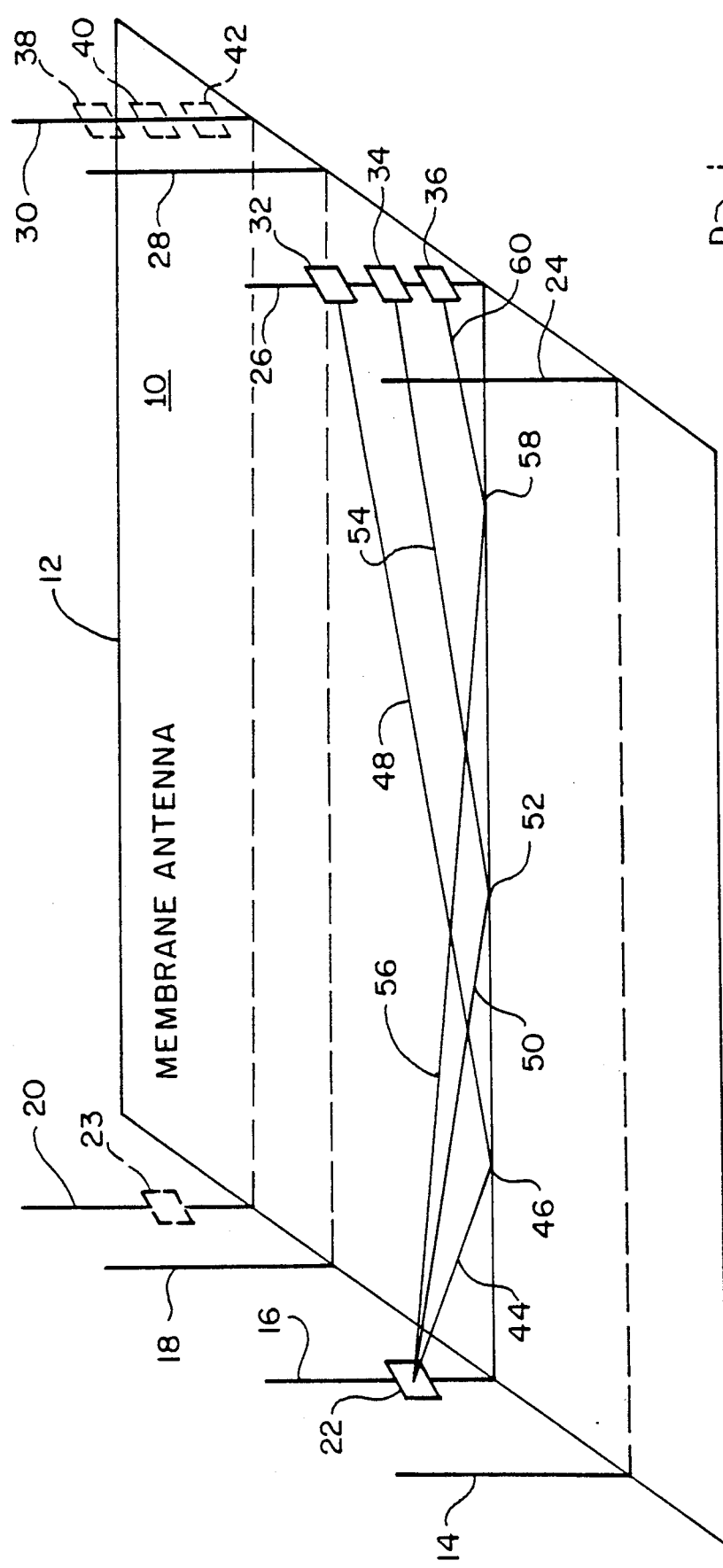
FIG. 1 is a perspective view of a membrane antenna having positional sensors mounted as a first embodiment of the present invention.

Referring to FIG. 1 the present invention is seen to be employed in connection with a membrane antenna 10 which is illustrated as being deployed. The periphery of the membrane antenna will normally have radiating elements secured thereto in a conventional fashion and are omitted from the figures in order to increase the clarity of the invention It is to be emphasized that the present invention is not the membrane antenna itself, but rather the sensor system for monitoring the antenna figure.

In the first embodiment of the invention illustrated in FIG. 1, a number of parallel upstanding posts 14, 16, 18, and 20 are illustrated. Four posts have been chosen for illustrative purposes only and a different number may be employed. Each post may have a conventional diode laser. For purposes of simplification only diode lasers 22 and 23 have been shown mounted on respective posts 16 and 20. Opposite the previously mentioned posts are four other posts 24, 26, 28, and 30. Each of the posts along one edge of the membrane antenna may be transversely located opposite a corresponding post on the opposite edge. Once again, the posts 24–30 may be different in number than the illustrated four posts. A plurality of polarization-sensitive silicon diode detector arrays 32, 34, and 36 are illustrated as mounted on the post 26. Similarly, arrays 38, 40, and 42 are mounted along post 30. It is to be understood that similar arrays are to be mounted along posts 24 and 28. Three arrays have been illustrated as connected to each post 26 and 30 but this number of arrays is merely illustrative.

In viewing FIG. 1 the diode laser 22 is a conventional component and directs polarized light (44) toward the membrane antenna where it is reflected at points 46, 52, and 58. The reflected polarized light from each of these points will then illuminate respective detector arrays 32, 34, and 36.

Figure 3:
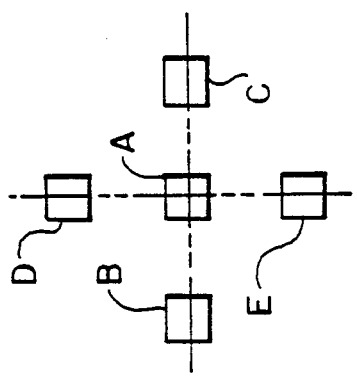
FIG. 3 is a diagrammatic view of polarization-sensitive diodes mounted in an array as employed in the first embodiment of the present invention.

The polarization-sensitive silicon diode detector arrays are preferably each comprised of five diodes symmetrically positioned as indicated by A-E in FIG. 3. With light reflected (48) from point 46 nominally impinging upon diode A, small deflections of the membrane antenna will register upward-downward or left-right displacement of the reflected laser beam to indicate motion of the membrane antenna 10. Similar detection occurs with reference to detector array 34 and reflection point 52 (for beams 50, 54). Likewise, detector array 36 is affected by the polarized light 56 reflected from point 58 as beam 60.

Diode lasers inherently produce 100 percent plane polarized radiation. The plane of polarization of the diode lasers must be set to be perpendicular to the plane of incidence of the reflection from the membrane surface of the antenna (i.e., the plane of incidence is defined by the perpendicular to the membrane surface at the point of reflection and the incident rays from the diode laser). The reason for this is that the reflection from the parallel component can go to zero at the polarizing angle for the dielectric surface, whereas the perpendicular component never goes to zero; as a matter of fact, the reflection of the perpendicular component is always very much stronger than the parallel component. At the polarizing angle for the membrane material, the perpendicular component becomes infinitely stronger than the parallel component.

Figure 2:
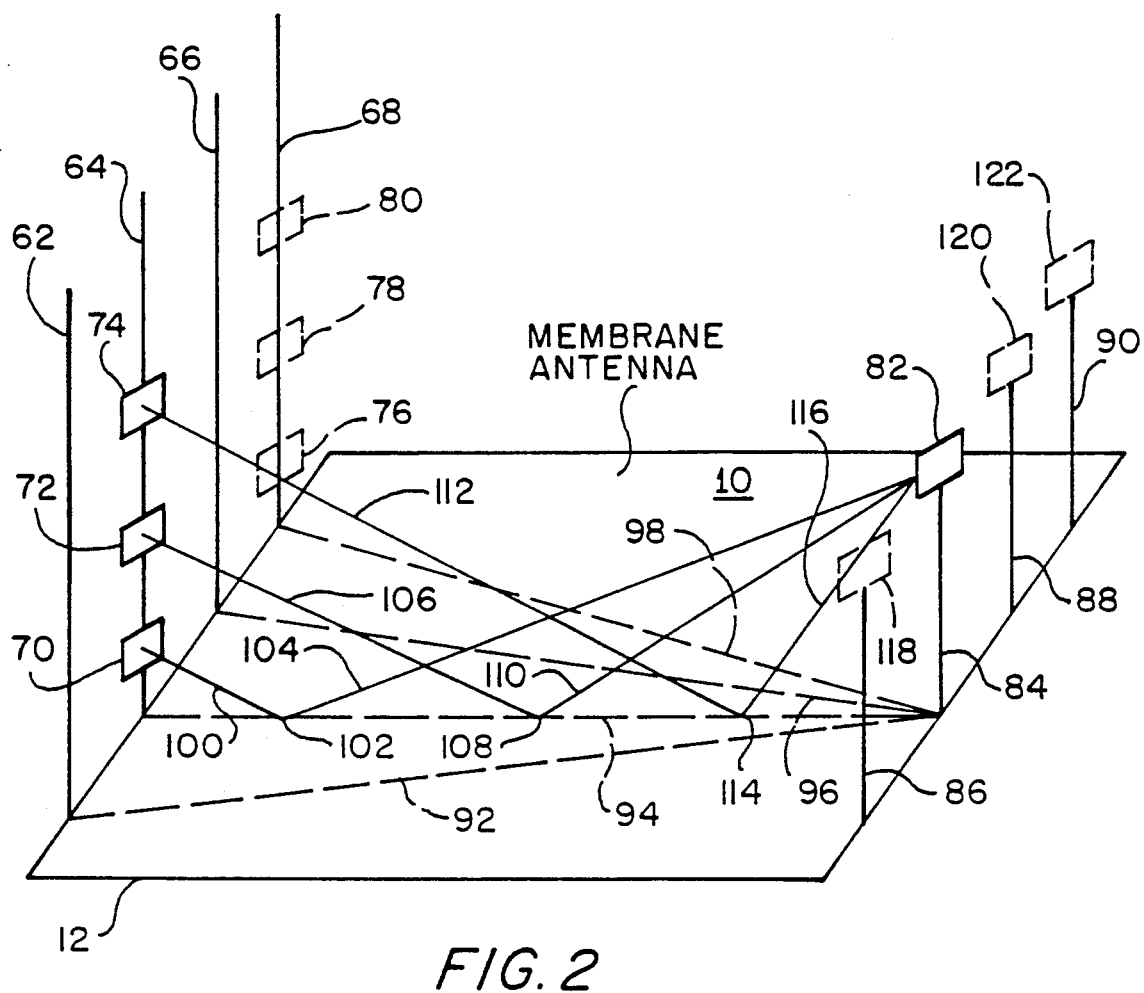
FIG. 2 is a perspective view of a membrane antenna having positional sensors mounted as a second embodiment of the present invention.

FIG. 2 illustrates a second embodiment of the present invention. Rather than using a single diode laser on each post, this embodiment employs a number of vertically spaced diode lasers. A single detector array is then used on each opposite post instead of the vertically spaced detector arrays of the first embodiment (FIG. 1). Thus, posts 62, 64, 66, and 68 each mount a plurality of diode lasers. Post 64 illustrates three lasers vertically spaced thereon and indicated by reference numerals 70, 72, and 74. Similarly, three vertically spaced diode lasers 76, 78, and 80 are mounted on post 68. Although not shown in the simplified view of FIG. 2, similarly vertically spaced diode lasers are secured to posts 62 and 66. Four posts are illustrated along an opposite transverse edge of the membrane antenna and are indicated by reference numerals 84, 86, 88, and 90. These are positioned in transverse alignment with the posts 62-68 and each carries an array of detectors. In a preferred embodiment of the present invention, the array is a 256×256 element CCD array. Four such arrays 82, 118, 120, and 122 are respectively secured to posts 84, 86, 88, and 90. By way of example, the array 82 receives polarized reflections from the diode lasers mounted on all of the oppositely positioned posts 62-68, as indicated by convergent lines 92, 94, 96, and 98. Similarly, each of the other arrays 118, 120, and 122 sequentially receives polarized reflection from all the diode lasers on the oppositely positioned posts. A number of reflection points 102, 108, and 114 are illustrated to explain the operation of the system in connection with respective diode lasers 70, 72, and 74. For example, diode laser 70 illustrates a polarized beam 100 being reflected from point 102 as polarized reflection 104 directed toward the array 82. Similarly, polarized beam 106 is emitted from diode laser 72; and after reflection at point 108, continues as polarized reflection 110 to the array 82. Finally, laser diode 74 directs a polarized beam 112 to reflection point 114 where its reflection 116 impinges upon the same array 82. As will be explained hereinafter, each of the diode lasers is turned on at a different moment in time by time coding so that its reflection data may be individually monitored. FIG. 2 also illustrates the utilization of additional CCD arrays 118, 120, and 122 on respective posts 86, 88, and 90. These arrays would monitor the polarized reflections from the diode laser sets. Reflection of the polarized laser radiation at each reflection point on the membrane antenna 10 to a particular CCD array is sensed to register the left-right and upward-downward displacement of the membrane antenna.

Figure 4:
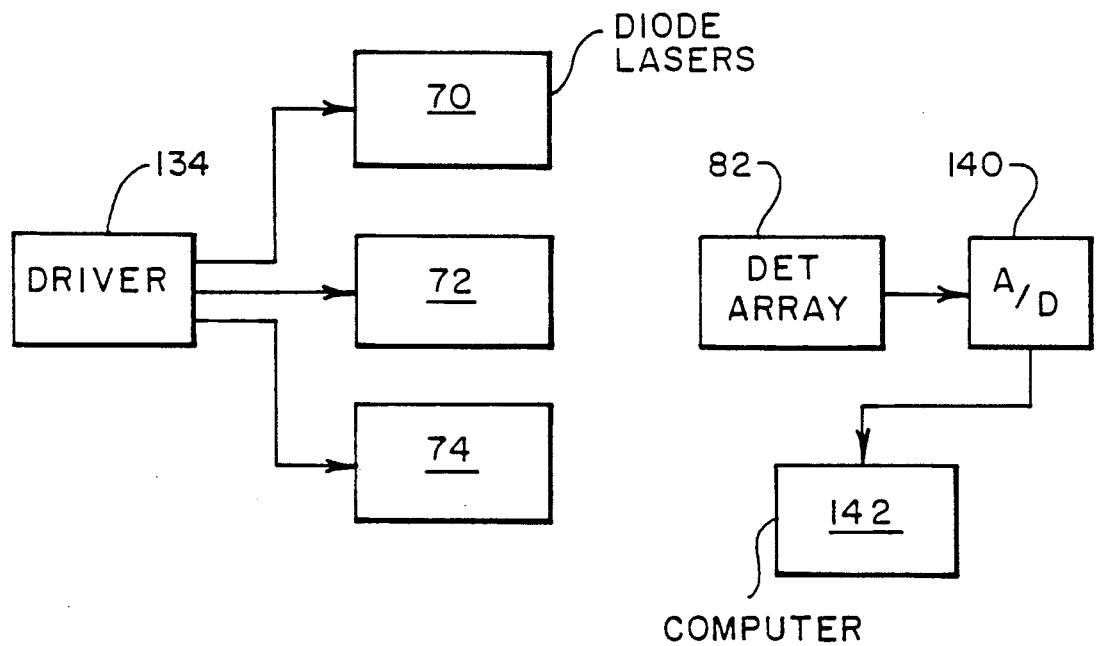
FIG. 4 is a simplified block diagram of the electronics employed with the present invention.

FIG. 4 is a basic block diagram of the electronics utilized in connection with the deployable membrane antenna 10. For example, the diode laser driver 134 sequentially drives each diode time-coded laser 70, 72, and 74 on post 64. The detector array 82 monitors the displacement of the reflection of each diode laser and analog-digital converter 140 converts the array output to digital format. The converter then feeds data to a computer 142 which performs a Fourier transformation of the data to transform the time domain displacement data from the array to two-dimensional spatial format. As the membrane antenna 10 undergoes slight vibration or other displacement, the changes of polarized reflection on various points of a CCD array registers the left-right and upward-downward displacement of the membrane antenna 10. The resulting digitally transformed data can then be used to electronically offset radar radiation data at various points of the antenna so as to give the antenna the effect of a planar radiating surface, or the data of the present invention may be employed in a servo system physically connected to various parts of the membrane antenna 10 for mechanically compensating for displacements of various points on the antenna in real time. Accordingly, the present invention is capable of satisfying a basic requirement for space-based antennas, namely the precise alignment of radiating elements and/or the reflector.

It should be understood that the invention is not limited to the exact details of construction shown and described herein for obvious modifications will occur to persons skilled in the art. The time-code modulation of the laser diodes must be rapid enough to permit deconvolving the membrane movement (i.e., 10 to 100 times the highest frequency to be sensed in the Fourier frequency domain).

We claim:

1. A system for monitoring deflections of a structure surface comprising:
   at least one source of polarized light directed toward the surface;
   at least one detector array located above the surface and opposite the source for detecting displacement of the polarized reflections as the surface deflects;
   means for converting analog data derived from the array to digital data; and
   means for performing a Fourier transformation of the digital data to transform the time domain displacement data from the array to two-dimensional spatial format.

2. The structure set forth in claim 1 wherein the source is a diode laser mounted above the surface; and further wherein the polarized reflections therefrom are monitored by a plurality of silicon diode arrays colinearly mounted generally orthogonally of the surface.

3. The structure set forth in claim 1 wherein the source comprises:
   a plurality of diodes colinearly mounted generally orthogonally of the surface; and
   further wherein the polarized reflections therefrom are monitored by at least one CCD array.

4. A system for monitoring antenna figure, the system comprising:
   a plurality of individual diode lasers respectively mounted on first supports over an antenna for producing polarized light;
   a plurality of second supports located opposite the first supports, each of which mounts a plurality of polarization-sensitive detector arrays over the antenna for detecting positional changes in real time, of reflections of polarized laser light, from the antenna, indicating changes in antenna figure;
   means for converting analog data derived from the arrays to digital data; and
   means for performing a Fourier transformation of the digital data to transform the time domain displacement data from the arrays to two-dimensional spatial format.

5. The structure set forth in claim 4 wherein each detector array comprises a central silicon diode and four additional silicon diodes arranged in quadrature.

6. A system for monitoring an antenna figure, the system comprising:
   a plurality of first supports located adjacent the antenna;
   a plurality of diode lasers mounted on each support for directing polarized light toward the antenna surface;
   a plurality of second supports located opposite the first supports, each of which mounts an individual polarization-sensitive detector array over the antenna for detecting positional changes in real time, of reflections in polarized light from the antenna, as the laser diodes are sequentially driven, the detected positional changes being indicative of changes in the antenna figure;
   means for converting analog data derived from the array to digital data; and
   means for performing a Fourier transformation of the digital data to transform the time domain displacement data from the array to two-dimensional spatial format.

7. The structure set forth in claim 6 wherein each detector array comprises a matrix of CCD devices.

* * * * *

UNITED STATES PATENT AND TRADEMARK OFFICE
CERTIFICATE OF CORRECTION

PATENT NO. : 5,054,928

DATED : October 8, 1991

INVENTOR(S) : Walter G. Egan, et al.

It is certified that error appears in the above-identified patent and that said Letters Patent is hereby corrected as shown below:

On the title page:
In the Abstract, line 6, after "array" insert --are converted to digital format and may then be used--.

Signed and Sealed this

Second Day of February, 1993

Attest:

STEPHEN G. KUNIN

*Attesting Officer*    Acting Commissioner of Patents and Trademarks